United States Patent [19]

Shields

[11] 4,348,523
[45] Sep. 7, 1982

[54] PREPARATION OF THIONAMIDE COMPOUNDS BY SULFURATION OF IMINES

[75] Inventor: Theodore C. Shields, Ashland, Ky.

[73] Assignee: Ashland Oil, Inc., Ashland, Ky.

[21] Appl. No.: 184,924

[22] Filed: Sep. 8, 1980

[51] Int. Cl.³ .................. C07D 295/10; C07C 155/02
[52] U.S. Cl. .................................... 544/399; 546/336; 564/74; 564/78
[58] Field of Search .................................. 564/74–78; 544/399; 546/336

[56] References Cited

U.S. PATENT DOCUMENTS 2,459,706  1/1949  King ..................................... 564/78
3,632,812  1/1972  Maier ................................... 564/78

OTHER PUBLICATIONS

Sandstrom et al., "Acta Chemica Scandinavia", vol. 21, (1967), 2254–2260.

Primary Examiner—Anton H. Sutto
Attorney, Agent, or Firm—Richard C. Willson, Jr.; Charles A. McCrae

[57] ABSTRACT

Useful thionamide compounds are prepared by reacting sulfur with imines of the structural formula:

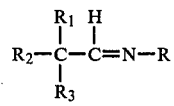

where R is an alkyl group of 1 to 18 carbon atoms and is other than a phenyl or cyclohexyl group, $R_1$ and $R_2$ are alkyl or phenyl groups of 1 to 18 carbon atoms, and $R_3$ is a phenyl group of 6 to 18 carbon atoms or is hydrogen, in the presence of a diol or triol compound. The total number of carbons in R, $R_1$, $R_2$, and $R_3$ does not exceed 36 in number.

17 Claims, No Drawings

PREPARATION OF THIONAMIDE COMPOUNDS BY SULFURATION OF IMINES

NATURE OF THE INVENTION

This invention relates to the formation of thionamide compounds by the reaction of sulfur with imine compounds.

BACKGROUND OF THE INVENTION

Thionamide compounds of the general structure:

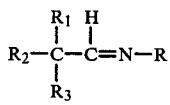

are not readily available industrially and are considered almost a rare chemical. Thionamide compounds are reported, however, to have potential uses in a variety of areas such as mining floatation additives, vulcanization, polymerization catalysts, electroplating, polymer stabilization, fiber fixatives, and as seed germinating agents. Thionamides are also suitable as chemical intermediates in the manufacture of other chemicals. I have now discovered a new and improved process for making thionamides by the reaction of free sulfur with imine compounds.

SUMMARY OF THE INVENTION

Briefly stated, this invention comprises a process for preparing thionamide compounds by reacting an imine having the following structural formula:

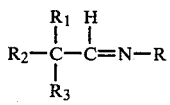

where R is an alkyl group of 1 to 18 carbon atoms, preferably of 1 to 8 carbon atoms, and is other than a cyclohexyl or phenyl group, $R_1$ and $R_2$ are each alkyl or phenyl groups of 1 to 18 carbon atoms, and $R_3$ is a phenyl group of 1 to 18 carbon atoms or is a hydrogen atom, with free sulfur in the presence of an immiscible alcohol compound. Preferably $R_1$ and $R_2$ are 1 to 6 carbon atoms each. The total number of carbons in R, $R_1$, and $R_2$, and $R_3$ does not exceed 36 in number.

DESCRIPTION OF THE INVENTION

As stated above, the process in general of this invention constitutes the preparation of a thionamide compound by reacting an imine having the structural formula:

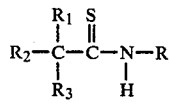

where R is a alkyl group, other than a cyclohexyl group or is other than a phenyl group, of 1 to 18 carbon atoms, $R_1$ and $R_2$ are alkyl or phenyl groups of 1 to 6 or 1 or 18 carbon atoms, and $R_3$ is hydrogen or a phenyl group of 1 to 18 carbon atoms, with elemental sulfur in the presence of a triol or diol.

Preferred imine compounds are those having the corresponding structural formulas:
2-ethylbutylidene isopropyl amine:

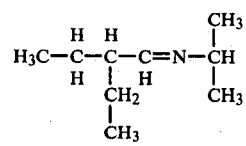

2-ethylbutylidene 2-ethylhexyl amine

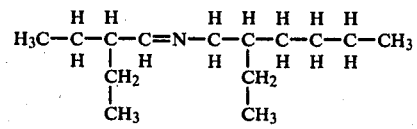

2-ethylhexylidene 2-ethylhexyl amine

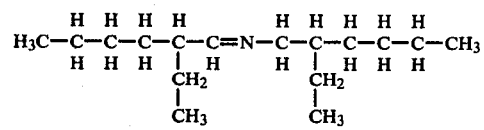

isobutylidene 2-ethylhexyl amine

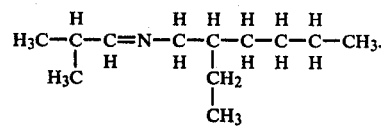

The sulfur utilized in the process can be in any form and preferably is in particulate form for ease in mixing. The third and necessary component of the reaction mixture is a diol or triol compound and preferably is selected from the group consisting of glycerol, ethylene glycol, 1,2-propane diol and triethanol amine. Any polyol or mono-ol can be used as long as it has sufficient polarity to make the alcohol phase and organic phase immiscible under the reaction conditions used. The sulfur is added to the reaction mixture preferably in a stoiciometric ratio of 1 gram atom of sulfur to 1 mole of the imine compound. The amount of diol or triol material included in the reaction mixture is between about 1 and 30% by weight per parts of total reaction mixture. Greater amounts could be used but is not economical. The reactants are mixed at room temperature preferably and then heated to a temperature of approximately 265° F. (130° C.) where the reaction becomes exothermic. The reaction is allowed to continue at an elevated temperature. The actual temperature of reaction is not critical other than that it should not be allowed to rise to a point where decomposition of the reactants or reaction product begins to occur. Ordinarily the temperature will not exceed 400° F. The reaction is conducted at atmospheric or near atmospheric pressure. When the reaction is completed, the reaction mixture is allowed to cool to reduce the temperature. It is then desirable to refine the thionamide product obtained by removing water and glycerin and any unreacted components.

One convenient method of purification constitutes first quenching the reaction mass in cold water and extracting the product in an organic solvent such as diethyl ether or pentane. After agitation the mixture is allowed to separate into two phases, an organic phase and an aqueous phase. The organic phase will contain the desired thionamide product. The thionamide product in the organic phase can then be decanted and the pentane or ether solvent removed by distillation. The resultant product ordinarily will be of a reddish amber appearance and is then ready for use for any of the uses outlined above.

EXAMPLE I

Isopropyl amine in the amount of 118 grams (2.0 gram moles) was slowly mixed at 10° C. in a reaction flask with 200 grams (2 gram moles) of 2-ethylbutyraldehyde over a 10 minute period. The reaction mixture was allowed to separate into an aqueous phase and an organic phase. The aqueous phase (33 grams) was discarded and the organic phase was dried by passing it through filter paper. Approximately 266 grams of organic product (considered to be 2-ethylbutenylidene isopropyl amine) was obtained. One hundred and twelve (112) grams (0.8 mole) of this material was then mixed with 100 grams of glycerol and heated with stirring to 90° C. Powdered sulfur in the amount of 30 grams (0.94 gram atoms) was then added to the mixture and heated further. At approximately 120° C. the sulfur melted into the glycerine phase and at 140° to 160° C. the evolution of heat was observed. The mixture was allowed to react for 30 minutes after which the mixture was cooled, quenched by the addition of 500 ml of ice water and extracted twice with 250 milliliters ether portions. The two 250 milliliter ether portions were combined, and passed through filter paper to be dried. The ether was then boiled away and the residue subjected to vacuum distillation at approximately 60° C. to produce 107 grams of an orange solid, deemed to be the desired product (N-isopropyl 2-ethylbutylthionamide). The product obtained when analyzed for sulfur showed 19% sulfur, which corresponds to 18.5% in the theoretical structure. NMR analysis showed the material to have the composition of N-isopropyl 2-ethylbutylthionamide.

EXAMPLE II

The procedure of Example I was followed except that glycerine was omitted in the second reaction. There was no evidence of the evolution of heat and the resultant product was a mixture of black products and water soluble white crystallane material which was not the desired product.

EXAMPLE III

Under the conditions described in the first reaction of Example I the compound, 2-ethylbutylidene 2-ethylhexyl amine, was prepared by reacting 258 grams (approximately 2.0 gram-moles) of 2-ethylhexyl amine and 200 grams (2.0 gram-moles) of 2-ethylbutyraldehyde. Approximately 404 grams of 2-ethylbutylidene 2-ethylhexyl amine were obtained.

NMR analysis indicated the product obtained conformed to the structure for 2-ethylbutylidene 2-ethylhexyl amine.

Three hundred and sixty (360) grams (1.7 gram-moles) of the product obtained was added to 50 grams of glycerol in a stirred flask and heated to 100° C. Sulfur powder (64 grams; 2.0 gram atoms) was added and the material heated further. At approximately 130° C. the sulfur melted into the glycerine phase and some evolution of heat was noted at 140° to 150° C. The final reaction temperature was 190° C. After a thirty minute reaction period, the reaction mixture was twice extracted with pentane (500 ml each). The first pentane fraction was distilled at atmospheric pressure and the second pentane fraction distilled under vacuum. During the distillation the pentane was removed first and then the thionamide product, at a higher temperature. The first cut resulted in a yield of 181 grams and the second in a cut of 134 grams. The sulfur content of the first cut product was 16.3% and that of the second 16.6% to be compared with a theoretical sulfur content of 16.3%.

EXAMPLE IV

The thionamide products obtained in Examples I and III were tested as wear additives in a concentration of 170 by weight in a 100 N lube oil stock using the Falex test procedure described in ASTM D-3233-73.

| Results were as follows: | Falex Results |
|---|---|
| Control (100 Valube Neutral) | (one-minute step-ups) OK at 300 lbs. jaw load, 7 lbs. torque; failed at 500 lbs. jaw load, 11 lbs. torque. |
| Product from Example I | OK at 500 lbs. jaw load, 12 lbs. torque; failed on step-up to 750 lbs. jaw load. |
| Product from Example III | OK at 500 lbs. jaw load, 12 lbs. torque; failed at 750 lbs. jaw load, 19 lbs. torque. |

These results were deemed acceptable.

EXAMPLE V

In further tests the compound prepared in Example I was added in the concentration shown below to 100 Cross Pole Oil and tested under ASTM-2267-67 (the four-ball wear test), ASTM D-2670-67 (Falex EP) and copper strip corrosion test. For comparison purposes corresponding concentrations of di-t-nonyl polysulfide (38.3% sulfur) were tested with following results:

| | FOUR-BALL WEAR TEST RESULTS | | | | | |
|---|---|---|---|---|---|---|
| Run # | Temp. °F. | Load kg. | % Additive | | % 100 Cross Pale | Test Scar, mm |
| 1 | 150 | 25 | 10 | (Ex. I) | 90 | .60 |
| 2 | 150 | 25 | 1 | (Ex. I) | 99 | .47 |
| 3 | 150 | 25 | .5 | (Ex. I) | 99.5 | .55 |
| 4 | 150 | 25 | — | | 100 | .78 |
| 5 | 150 | 25 | 10 | (Ex. I) | 90 | .60 |
| 6 | 150 | 25 | 1 | (Ex. I) | 99 | .44 |
| 7 | 150 | 25 | .5 | (Ex. I) | 99.5 | .57 |
| 8 | 150 | 25 | — | | 100 | .81 |
| 9 | 150 | 25 | 10 | DTNPS | 90 | 1.22 |
| 10 | 150 | 25 | 1 | DTNPS | 99 | .51 |
| 11 | 150 | 25 | .5 | DTNPS | 99.5 | .45 |
| 12 | 150 | 25 | 10 | DTNPS | 90 | 1.23 |
| 13 | 150 | 25 | 1 | DTNPS | 99 | .50 |
| 14 | 150 | 25 | .5 | DTNPS | 99.5 | .46 |
| 1 | 250 | 25 | 10.0 | (Ex. I) | 90.0 | .80 |
| 2 | 250 | 25 | 1.0 | (Ex. I) | 99.0 | .54 |
| 3 | 250 | 25 | 0.5 | (Ex. I) | 99.5 | .62 |
| 4 | 250 | 25 | — | | 100.0 | 1.01 |
| 5 | 250 | 25 | 10.0 | (Ex. I) | 90.0 | .80 |
| 6 | 250 | 25 | 1.0 | (Ex. I) | 99. | .60 |
| 7 | 250 | 25 | 0.5 | (Ex. I) | 99.5 | .64 |
| 8 | 250 | 25 | — | | 100.0 | 1.02 |
| 9 | 250 | 25 | 10.0 | DTNPS | 90.0 | 1.45 |
| 10 | 250 | 25 | 1.0 | DTNPS | 99.0 | .54 |
| 11 | 250 | 25 | 0.5 | DTNPS | 99.5 | .48 |

-continued

FOUR-BALL WEAR TEST RESULTS

| Run # | Temp. °F. | Load kg. | % Additive | | % 100 Cross Pale | Test Scar, mm |
|---|---|---|---|---|---|---|
| 12 | 250 | 25 | 10.0 | DTNPS | 90.0 | 1.50 |
| 13 | 250 | 25 | 1.0 | DTNPS | 99.0 | .56 |
| 14 | 250 | 25 | 0.5 | DTNPS | 99.5 | .47 |

FALEX EP TEST RESULTS

Run #1
 90% 100 Cross Pale Oil
 10% (Component of Example I)
  OK at 1000 lbs. Jaw Load and 17.5 lbs. Torque
  Failed at 1250 lbs. Jaw Load and 22.0 lbs. Torque
Run #2
 99% 100 Cross Pale Oil
 1% (Component of Example I)
  OK at 1500 lbs. Jaw Load and 33.0 lbs. Torque
  Failed at 1600 lbs. Jaw Load and 40.0 lbs. Torque
Run #3
 99.5% 100 Cross Pale Oil
 0.5% (Component of Example I)
  OK at 1250 lbs. Jaw Load and 26.0 lbs. Torque
  Failed at 1450 lbs. Jaw Load and 32.0 lbs. Torque
Run #4
 100% 100 Cross Pale Oil
  OK at 1000 lbs. Jaw Load and 20.5 lbs. Torque
  Failed at 1200 lbs. Jaw Load and 25.0 lbs. Torque
Run #5
 90% 100 Cross Pale Oil
 10% DTNPS
  OK at 1750 lbs. Jaw Load and 49.0 lbs. Torque
  Failed at 1800 lbs. Jaw Load and 49.5 lbs. Torque
Run #6
 99% 100 Cross Pale Oil
 1% DTNPS
  OK at 1500 lbs. Jaw Load and 47.5 lbs. Torque
  Failed at 1600 lbs. Jaw Load and 49.0 lbs. Torque
235 Run #7
 99.5% 100 Cross Pale Oil
 0.5% DTNPS
  OK at 1250 lbs. Jaw Load and 26.5 lbs. Torque
  Failed at 1450 lbs. Jaw Load and 50.0 lbs. Torque.

COPPER CORROSION STRIP TEST

| Run # | Blend | Room Temperature | 212° F. |
|---|---|---|---|
| 1 | 100.0% Cross Pale Oil | 1a | 1a |
| 2 | 99.0% 100 Cross Pale Oil 1.0% Ted's Compound | 1a | 1a |
| 3 | 99.5% 100 Cross Pale Oil 0.5% Ted's Compound | 1a | 1a |
| 4 | 99.0% 100 Cross Pale Oil 1.0% DTNPS | 1a | 4a |
| 5 | 99.5% 100 Cross Pale Oil 0.5% DTNPS | 1a | 4a |

*A corrosion rating of "1a" indicates no detectable corrosion; a "4a" rating indicates a high degree of corrosion.

These tests indicate the utility of the compounds of the invention in improving wear and extreme pressure features of lubricants. The side effects of corrosion are substantially reduced.

It has been determined that the presence of a polar solvent is not necessary if the imine compound has incorporated within it sufficient polarity. Specifically imine compounds meeting this requirement have the structural formula:

$$Y-\underset{Z}{\overset{X}{C}}-\overset{H}{C}=N-Q$$

where the total of the atomic weights of X, Y, Z and Q is less than 300. The imine compound must further contain at least one of the following groups: hydroxy, mercapto, ether, thioether, amido, thionamido, sulfoxy, sulfonyl, tertiary amine, secondary amine or pyridyl amine. Preferably X, Y, Z and Q contain atoms selected from the group consisting of hydrogen, carbon, oxygen, sulfur and secondary, tertiary and pyridyl nitrogen atoms.

Imine compounds and their corresponding structural formulas meeting this requirement are:

2-ethylhexylidene 2,2-dimethyl-3-dimethylaminopropyl amine (A)

$$H_3C-\underset{H}{\overset{H}{C}}-\underset{H}{\overset{H}{C}}-\underset{H_2C-CH_3}{\overset{H}{C}}-\underset{H}{\overset{H}{C}}-\overset{H}{C}=N-\underset{H}{\overset{H}{C}}-\underset{CH_3}{\overset{CH_3}{C}}-\underset{CH_3}{\overset{H}{C}}-N-CH_3$$

2-isobutylidene 2-methoxyethyl amine (B)

$$H_3C-\underset{CH_3}{\overset{H}{C}}-\overset{H}{C}=N-\underset{H}{\overset{H}{C}}-\underset{H}{\overset{H}{C}}-O-CH_3$$

2-ethylhexylidene 2(N-piperidino)ethyl amine (C)

$$H_3C-\underset{H}{\overset{H}{C}}-\underset{H}{\overset{H}{C}}-\underset{H}{\overset{H}{C}}-\underset{\underset{CH_3}{CH_2}}{\overset{H}{C}}-\overset{H}{C}=N-\underset{H}{\overset{H}{C}}-\underset{H}{\overset{H}{C}}-N\begin{array}{c}C-C\\H_2\ H_2\\ \\C-C\\H_2\ H_2\end{array}NH$$

(3-pyridyl)methylidene isopropyl amine (D)

$$H_3C-\underset{CH_3}{\overset{H}{C}}-N=\underset{H}{\overset{H}{C}}-C\begin{array}{c}C-N\\H\\ \\C=C\\H\ H\end{array}CH$$

2-ethylhexylidene 1,1-dimethylolpropyl amine (E)

$$H_3C-\underset{H}{\overset{H}{C}}-\underset{H}{\overset{H}{C}}-\underset{H}{\overset{H}{C}}-\underset{\underset{CH_3}{CH_2}}{\overset{H}{C}}-\overset{H}{C}=N-\underset{\underset{OH}{CH_2}}{\overset{\overset{CH_3}{HCH}}{C}}-\underset{H}{\overset{H}{C}}-OH$$

EXAMPLE IV

Each of the above amine derivatives A, B, C, D, and E was prepared in the laboratory. The prepared derivatives were then reacted with elemental sulfur on a basis of one gram mole of derivative per gram atom of sulfur. Reaction began when a mixture of a reactant was heated to about 110° C. Reaction continued while the temperature rose to 140° C. After reaction was deemed complete, the mixture was cooled and extracted with ether. The ether fraction was then distilled to remove the ether. The residue was the desired end product.

I claim:

1. A method of making thionamides comprising reacting an imine having the structural formula:

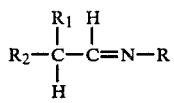

where R is an alkyl group, other than a cyclohexyl group, of 1 to 18 carbon atoms, $R_1$ and $R_2$ are each phenyl groups or alkyl groups of 1 to 18 carbon atoms, and the sum of the carbon atoms in $R_1$, and $R_2$ is less than 36, with free sulfur in the presence of an immiscible polyol compound.

2. The process of claim 1 wherein the reaction product obtained is purified by removing unreacted starting material.

3. The process of claim 1 wherein the imine is selected from the group having the following structural formula:

2-ethylbutylidene isopropyl amine:

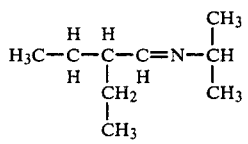

2-ethylbutylidene 2-ethylhexyl amine

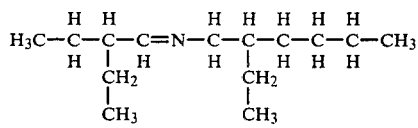

2-ethylhexylidene 2-ethylhexyl amine

H H H H       H H H H H
H₃C—C—C—C—C—C=N—C—C—C—C—C—CH₃
   H H H | H     H | H H H
         CH₂      CH₂
         |        |
         CH₃      CH₃ isobutylidene 2-ethylhexyl amine

H           H H H H H
H₃C—C—C=N—C—C—C—C—C—CH₃.
    | H       H | H H H
   H₃C          CH₂
                |
                CH₃

4. The process of claim 1 wherein the reaction between said imine and said sulfur is carried out at a temperature less than about 400° F.

5. The process of claim 1 wherein the polyol is selected from the group consisting of glycerol, ethylene glycol 1,2-propylene glycol, and trimethylene glycol.

6. The method of claim 1 wherein R is an alkyl group of 1 to 12 carbon atoms.

7. The product produced by the process of 3.

8. The process of claim 1 wherein the ratio of sulfur to imine is about 1 gram atom per gram mole respectively.

9. The process of claim 1 wherein the concentration of diol or triol used in said reaction mixture is between about 1 and about 30 parts by weight per 100 parts of reaction mixture.

10. A method of making thionamides comprising reacting an imine having the structural formula:

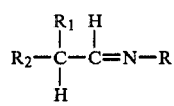

where R is an alkyl group, other than a cyclohexyl group, of 1 to 18 carbon atoms, $R_1$ and $R_2$ are each phenyl groups or alkyl groups of 1 to 18 carbon atoms and the sum of the carbon atoms in $R_1$ and $R_2$ is less than 36, the total of the atomic weights of R, $R_1$, and $R_2$ is less than 300 and said imine contains at least one substituent selected from the group consisting of hydroxy, mercapto, ether, thioether, amido, thionamido, sulfoxy, sulfonyl, tertiary amine, secondary amine or pyridyl amine, and wherein addition of immiscible alcohol compound is omitted.

11. The method of claim 10 wherein R, $R_1$, and $R_2$ contain atoms selected from the group consisting of hydrogen, carbon, oxygen, sulfur and secondary, tertiary and pyridyl nitrogen atoms.

12. The process of claim 10 wherein said imine has the structural formula:

H H H H H    H  CH₃ H
H₃C—C—C—C—C—C=N—C—C—C—N—CH₃.
   H H H |       H  | H  |
        H₂C—CH₃     CH₃ CH₃

13. The process of claim 10 wherein said imine has the structural formula:

H H     H H
H₃C—C—C=N—C—C—O—CH₃.
   |       H H
   CH₃

14. The process of claims 10 wherein said imine has the structural formula:

H₂ H₂
                                C—C
    H H H H H   H H        /       \
H₃C—C—C—C—C—C=N—C—C—N        NH.
    H H H |     H H        \       /
         CH₂                 C—C
         |                  H₂ H₂
         CH₃

15. The process of claim 10 wherein said imine has the structural formula:

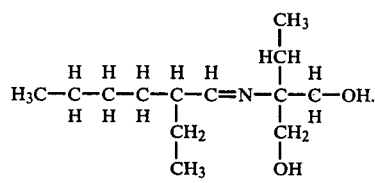
16. The process of claim 10 wherein said imine has the structural formula:
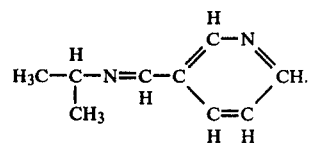
17. The product produced by the process of claims 10, 11, 12, 13, 14, 15, or 16.
* * * * *